(12) United States Patent
Lu et al.

(10) Patent No.: US 8,414,552 B2
(45) Date of Patent: Apr. 9, 2013

(54) NEGATIVE PRESSURE BANDAGE

(75) Inventors: Wei-Hua Lu, Neipu Hsiang (TW);
Yung-Chuan Chen, Neipu Hsiang (TW); Ting-Lung Chiang, Neipu Hsiang (TW)

(73) Assignee: National Pingtung University of Science & Technology, Pingtung County (TW)

( * ) Notice: Subject to any disclaimer, the term of this patent is extended or adjusted under 35 U.S.C. 154(b) by 337 days.

(21) Appl. No.: 12/815,581

(22) Filed: Jun. 15, 2010

(65) Prior Publication Data
US 2011/0009839 A1    Jan. 13, 2011

(30) Foreign Application Priority Data

Jul. 13, 2009   (TW) ................. 98123646 A

(51) Int. Cl.
*A61M 1/00* (2006.01)
(52) U.S. Cl. ........ 604/319; 604/187; 604/192; 604/268; 604/290; 604/296; 604/300; 604/304; 604/305; 604/312
(58) Field of Classification Search .......... 604/316, 604/318, 319
See application file for complete search history.

(56) References Cited

U.S. PATENT DOCUMENTS

| | | | |
|---|---|---|---|
| 5,759,570 A * | 6/1998 | Arnold | 424/443 |
| 7,381,859 B2 | 6/2008 | Hunt et al. | |
| 7,553,306 B1 | 6/2009 | Hunt et al. | |
| 7,648,488 B2 | 1/2010 | Smith et al. | |
| 7,678,102 B1 | 3/2010 | Heaton | |
| 7,901,372 B2 * | 3/2011 | Daneshvar | 602/62 |
| 2008/0167593 A1 * | 7/2008 | Fleischmann | 602/48 |

FOREIGN PATENT DOCUMENTS

| | | |
|---|---|---|
| JP | 360334 Z | 12/1967 |
| TW | 200920418 | 5/2009 |

* cited by examiner

*Primary Examiner* — Tatyana Zalukaeva
*Assistant Examiner* — Ilya Treyger
(74) *Attorney, Agent, or Firm* — Alan Kamrath; Kamrath IP Lawfirm, P.A.

(57) ABSTRACT

A pressure bandage includes a banding porting, at least one infiltration and at least one fixing member. The banding portion includes at least one recession formed in one side of the banding portion, at least one tube having first and second ends, and at least one check valve mounted in the second end of the tube. The first end of the tube is connected to the recession. The infiltration is coupled on the inner surface of the recession of the banding portion. The fixing member fixes the banding portion to a treatment part.

6 Claims, 8 Drawing Sheets

NEGATIVE PRESSURE BANDAGE

BACKGROUND OF THE INVENTION

1. Field of the Invention

The present invention generally relates to a negative pressure bandage and, more particularly, to a negative pressure bandage that allows free movement of the user using the negative pressure bandage.

2. Description of the Related Art

As known by the technician who is familiar with vacuum sealing therapy, wound healing is a process of self-repairment of skin after trauma, which may be categorized into hemostasis, inflammatory, proliferative and remodeling phases. In the inflammatory phase, some bacteria are cleaned and removed leading to the migration and division of involved epithelium or subcutaneous tissues. As a result, the blood flow may increase in order to bring about a significant amount of releasing factors for initiating the proliferation of cells. However, in the inflammatory phase, the blood flow in the damaged blood vessels may be interfered by the clotting taking place in the capillaries. In this situation, a clean treatment and a tissue reconstruction process are needed to advance the cellular proliferation. On the other hand, the wound repairment may also be interrupted due to the tissue timidity caused by serious infection of the wound. As a result, the lack of oxygen and nutrition in the epithelium cells and subcutaneous tissue around the wound may result in a poor resistance of the wound to bacteria infection, leading to a postponement of wound healing.

Therefore, in conventional study, staples or closure treatment, as well as negative pressure wound therapy, are usually used to promote the process of healing in acute or chronic wounds. Among them, the negative pressure wound therapy is used to create a sub-atmospheric pressure on the local wound environment, which shows better utility and effects.

A conventional negative pressure bandage, published in Taiwan Patent No. 200920418 and entitled "Detachable pump and the negative pressure wound therapy system using the same", includes a top module and a bottom module. The top module includes a motor set and a top elastic member. The bottom module includes a base having an inlet and an outlet, at least one first check valve positioned in the inlet, at least one second check valve positioned in the outlet, a diaphragm and a bottom elastic member. With the first and second check valves of the aforesaid system, spent liquid can be prevented from flowing back to a wound section or the base. The motor set is adapted to push the top elastic member, and the resilience of the top elastic member is countered with the resilience of the bottom elastic member, such that the diaphragm element can be propelled to generate a vacuuming force. By incorporating the aforesaid detachable pump and a banding portion made of an absorbent material into a negative pressure wound therapy system, the spent liquid of a wound is drawn by the pump and absorbed directly by the banding portion.

The conventional negative pressure bandage above has complex elements. On the other hand, a user is limited from free movement due to the position of the detachable pump. Thus, the conventional negative pressure bandage must be removed when the free movement of the user is desired. As a result, a treatment part of the user can not be maintained in the negative pressure status, resulting in an inconvenient use of the negative pressure bandage.

SUMMARY OF THE INVENTION

An objective of the present invention is to provide a negative pressure bandage which allows free movement of a user using the pressure bandage.

Another objective of the present invention is to provide a negative pressure bandage which allows connecting with a pump when the pressure difference between the negative pressure in the negative pressure bandage and the atmospheric pressure becomes small, maintaining the negative pressure bandage in a negative pressure status.

A further objective of the present invention is to provide a negative pressure bandage that has fewer elements to enhance assembling convenience and to reduce manufacturing costs.

Still another objective of the present invention is to provide a negative pressure bandage that has an excellent air-tightness between a banding portion and a body portion near a treatment part of the user.

The invention discloses a negative pressure bandage comprising a banding porting, at least one infiltration and at least one fixing member. The banding portion includes at least one recession formed in one side of the banding portion, at least one tube having first and second ends, and at least one check valve mounted in the second end of the tube. The first end of the tube is connected to the recession. The infiltration is coupled on the inner surface of the recession of the banding portion. The fixing member fixes the banding portion to a treatment part.

BRIEF DESCRIPTION OF THE DRAWINGS

The present invention will become more fully understood from the detailed description given hereinafter and the accompanying drawings which are given by way of illustration only, and thus are not limitative of the present invention, and wherein.

Figure 1:
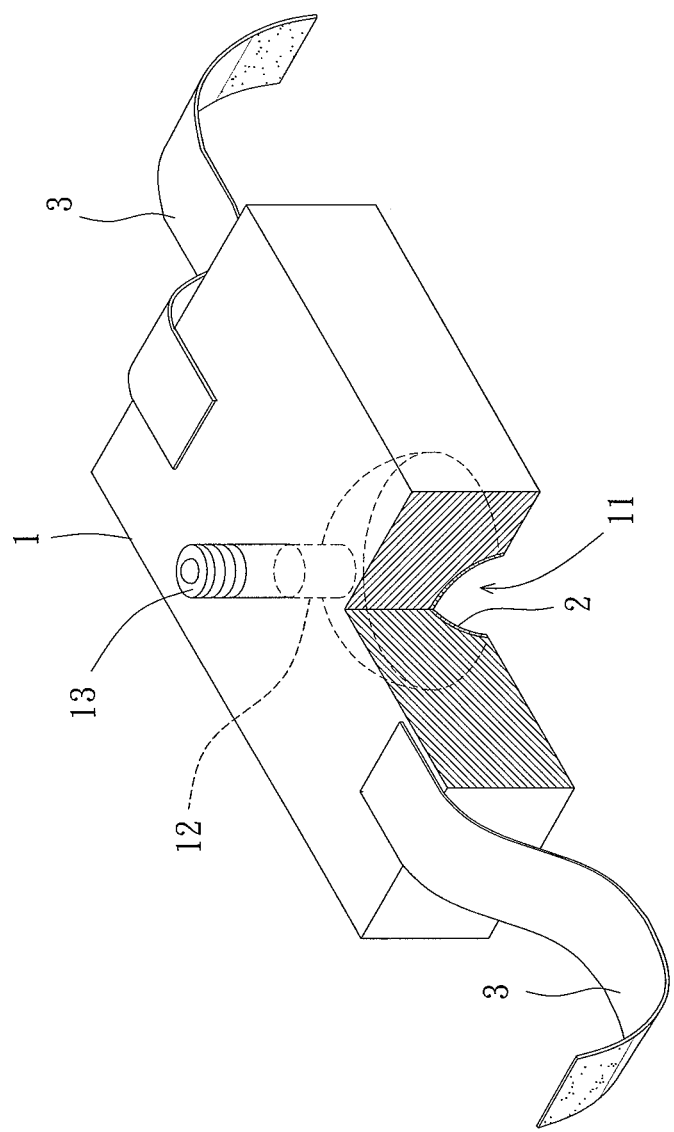
FIG. 1 shows a cross sectional view of a negative pressure bandage according to a first embodiment of the invention.

In the various figures of the drawings, the same numerals designate the same or similar parts. Furthermore, when the terms "first", "second", "positive", "negative" "outer", "inner" and similar terms are used hereinafter, it should be understood that these terms have reference only to the structure shown in the drawings as it would appear to a person viewing the drawings and are utilized only to facilitate describing the invention.

DETAILED DESCRIPTION OF THE INVENTION

Figure 2:
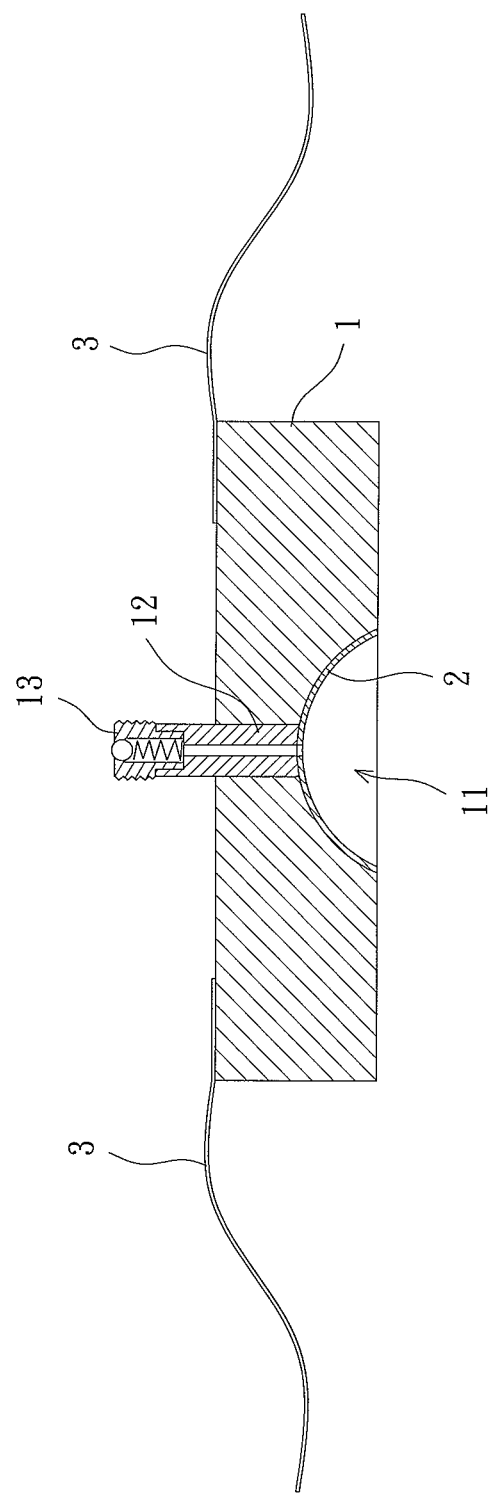
FIG. 2 shows a side cross sectional view of the negative pressure bandage according to the first embodiment of the invention.

Referring to FIGS. 1 and 2, a negative pressure bandage is disclosed according to a first embodiment of the invention. The negative pressure bandage comprises a banding portion 1, at least one infiltration 2 covered on the banding portion 1, and at least one fixing member 3 adapted to fix the banding portion 1 on a treatment part 92 of a body portion 94 of a user requiring negative pressure treatment.

In the preferred form shown, the banding portion 1 is made of a shapeable sponge, an elastic bandage, or the like. The banding portion 1 can be of any desired shape and size. The banding portion 1 includes at least one recession 11, a tube 12 and a check valve 13. The recession 11 is formed in one side of the banding portion 1 and faces the treatment part 92 of the user. The recession 11 can be of any shape and size corresponding to the shape and size of the treatment part 92. The tube 12 is embedded in the banding portion 1. The tube 12 has a first end 121 connected with the at least one recession 11 and a second end 122 extending out of the banding portion 1. The check valve 13 is mounted on the second end 122 of the tube 12. The check valve 13 is adapted to connect with a decompressing device 4 via a conduit 41, such that the recession 11 can be decompressed to a negative pressure status by the decompressing device 4.

The infiltration 2 is arranged on the inner surface of the recession 11 of the banding portion 1 to prevent air from flowing into the recession 11 through the porous structure of banding portion 1. The first end 121 of the tube 12 extends through the infiltration 2 to communicate with the recession 11. When the banding portion 1 is placed on the treatment part 92 of the user requiring negative pressure treatment, and when the decompressing device 4 is operated, the pressure in the recession 11 can be reduced to a desired pressure smaller than atmospheric pressure due to the isolation of the infiltration 2.

The fixing member 3 can be any element adapted to fix the banding portion 1 on the treatment part 92 of the user requiring the negative pressure treatment. In the first embodiment shown, the fixing member 3 may be two straps respectively having a hook fastener and a loop fastener releasably engaged with the hook fastener, such that the straps can wrap around the body portion 94 of the user and define a space receiving the body portion 94 with the treatment part 92.

Figure 3:
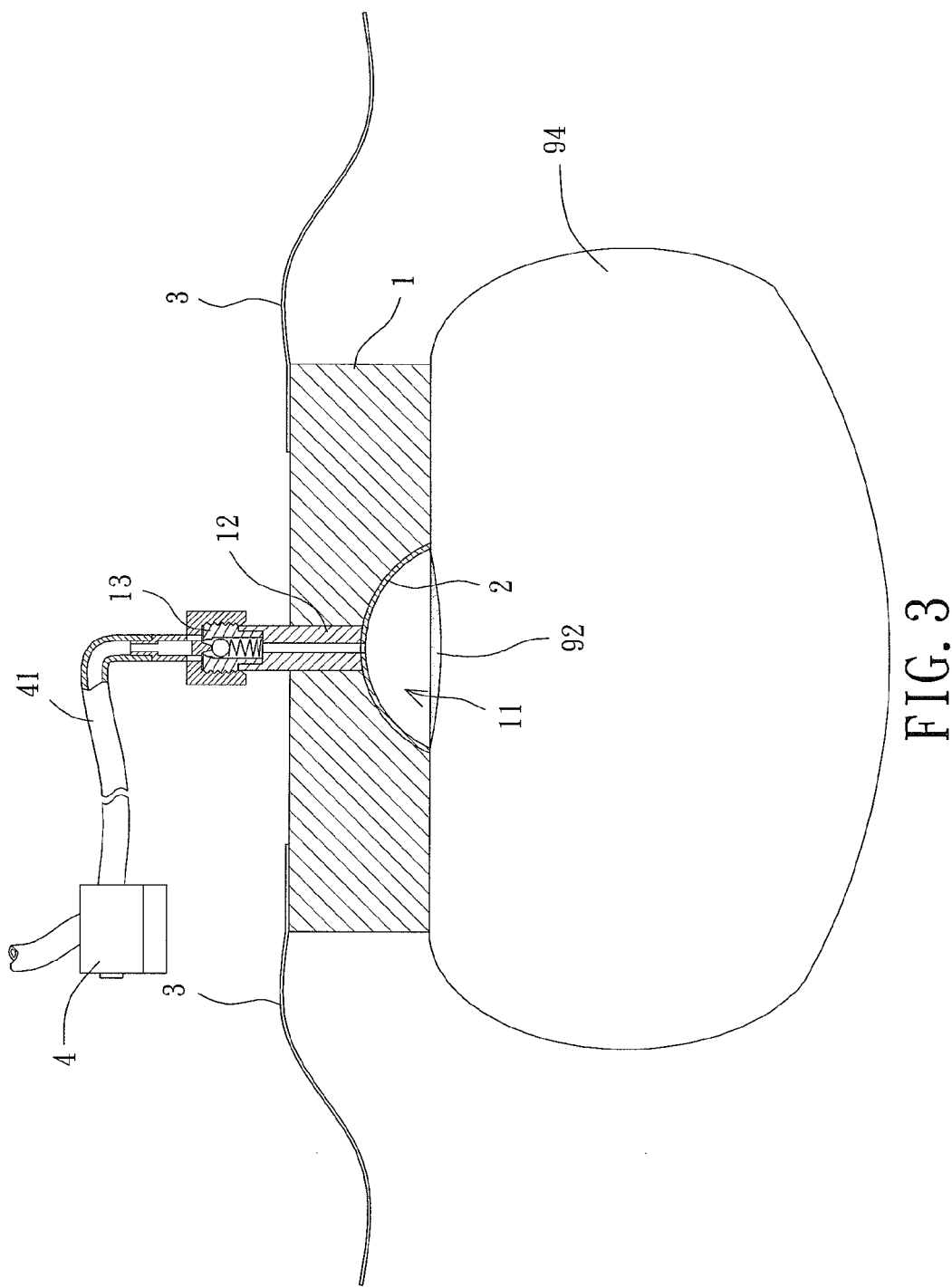
FIG. 3 shows a side cross sectional view of the negative pressure bandage of FIG. 1 which is mounted to a treatment part and connected to a decompressing device.
Figure 4:
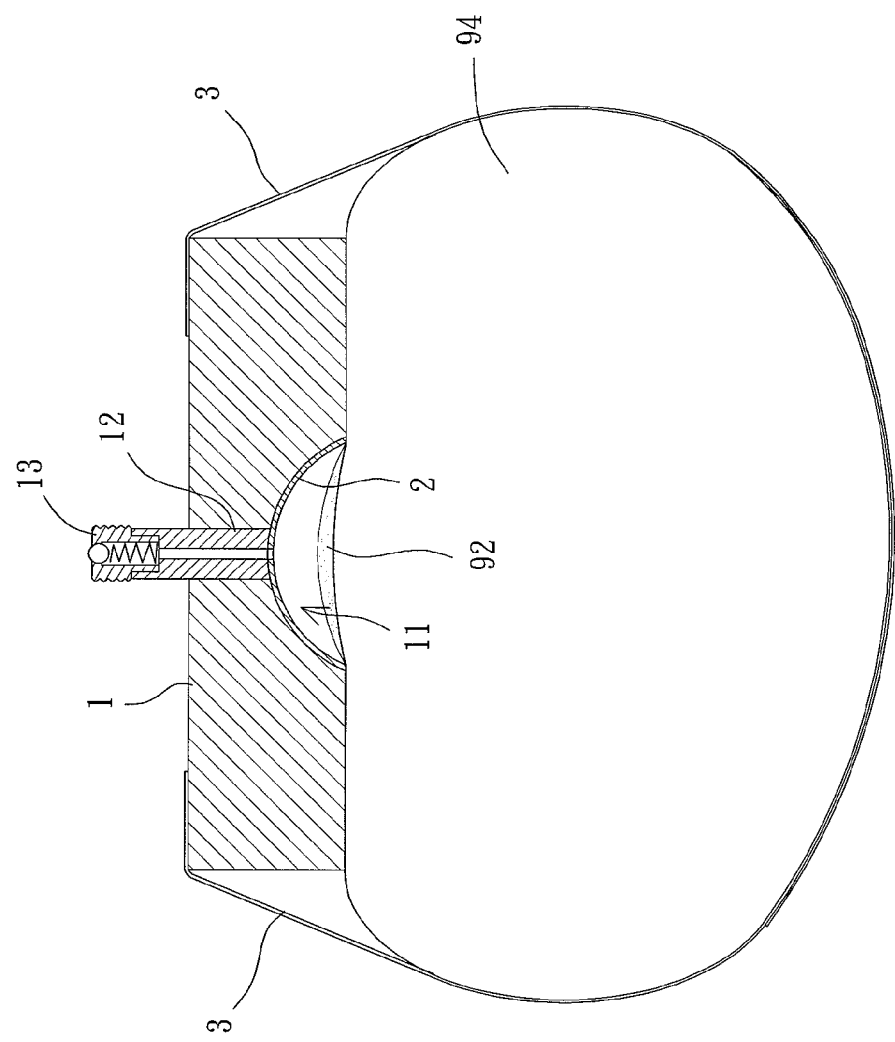
FIG. 4 shows a side cross sectional view similar to FIG. 3, illustrating maintaining of a negative pressure status.

Referring to FIGS. 3 and 4, the decompressing device 4 may be a pump. The decompressing device 4 is connected with the check valve 13 of the banding portion 1 by the conduit 41 such that the pressure of the recession 11 can be reduced through the operation of the decompressing device 4.

FIG. 4 shows a use of the negative pressure bandage according to the preferred teachings of the present invention. Firstly, the treatment part 92 of the user requiring the negative pressure treatment is covered by the recession 11 of the banding portion 1, with the coverage of the recession 11 being larger than that of the treatment part 92 to allow the full coverage of areas including the treatment part 92 and the healthy tissues surrounding the treatment area 92. Furthermore, a protection agent is coated between the body portion 94 around the treatment part 92 and the surface of the banding portion 1 around the recession 11 when the treatment part 92 of the user is covered by the banding portion 1. Secondly, the banding portion 1 is fixed to the treatment part 92 of the user via the fixing member 3.

When the decompressing device 4 is operated, the air in the recession 11 is drawn out of the recession 11 so that the pressure in the recession 11 can be reduced to a desired level smaller than the atmospheric pressure. In addition, the pressure difference between the atmospheric pressure and the pressure in the recession 11 can be maintained or adjusted by operating the decompressing device 4.

If the user is intended to move a distance beyond the length of the conduit 41, the check valve 13 of the banding portion 1 can be detached from one end of the conduit 41 after the decompressing device 4 decompresses the recession 11 to a negative pressure status. Therefore, the negative pressure bandage of the present invention can allow the free movement of the user while using the negative pressure bandage. Since the check valve 13 is adapted to prevent air from flowing into the recession 11, the pressure in the recession 11 can be maintained under a negative pressure status. The check valve 13 also can be reconnected with the conduit 41 in order to adjust the negative pressure applied to the treatment part 92 when the pressure difference between the atmospheric pressure and the pressure imparted by the negative pressure bandage to the treatment part 92 becomes small.

Figure 5:
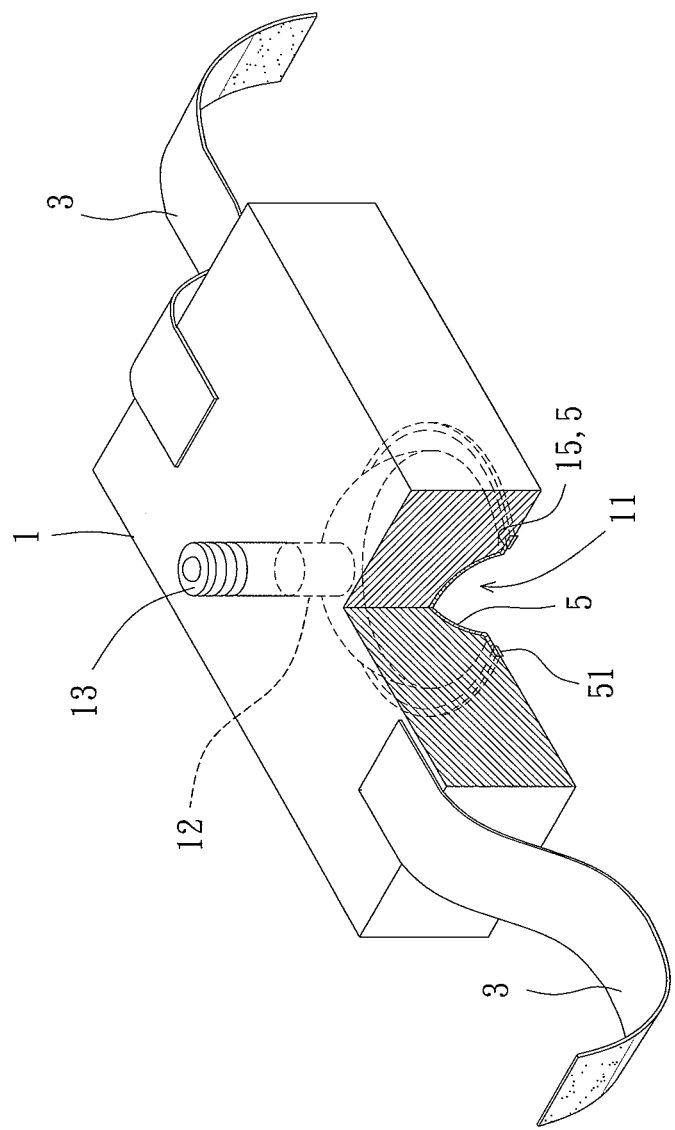
FIG. 5 shows a cross sectional view of the negative pressure bandage according to a second embodiment of the invention.
Figure 6:
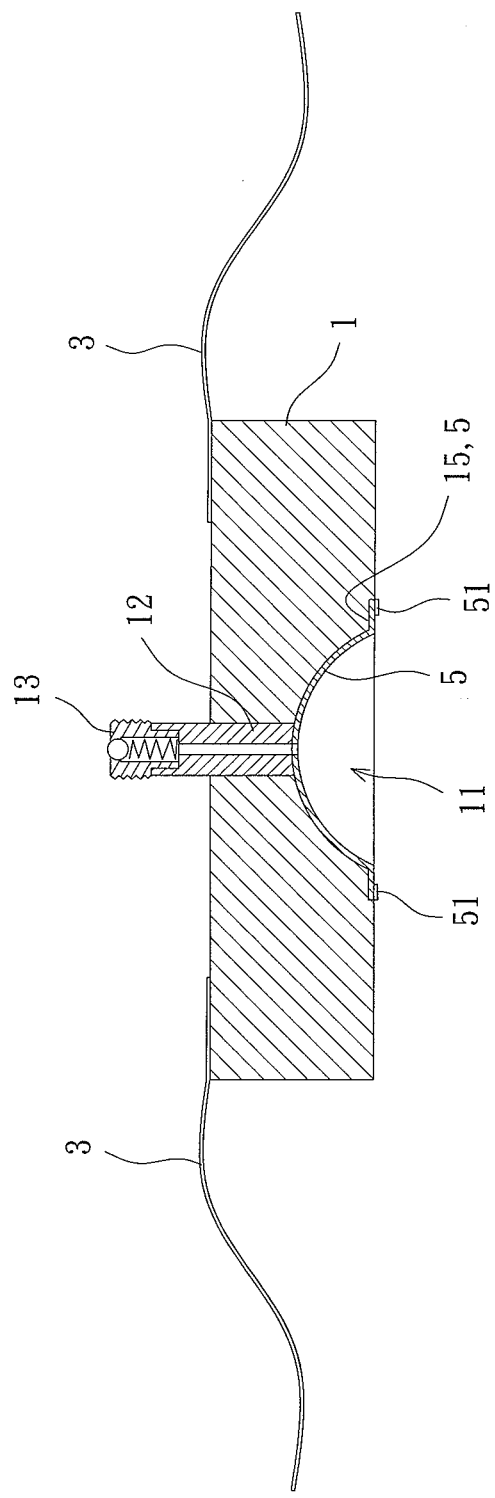
FIG. 6 shows a side cross sectional view of the negative pressure bandage according to the second embodiment of the invention.

Referring to FIGS. 5 and 6, a negative pressure bandage is disclosed according to a second embodiment of the present invention is shown. In comparison with the first embodiment, what is different is that the recession 11 of the banding portion 1 further includes an extending groove 15 formed on the periphery of the recession 11, and an infiltration 5 is covered on the inner surface of the recession 11 and the extending groove 15. The infiltration 5 includes an adhesive layer 51 preferably made of an adhesive agent not harmful to the skin tissue around the treatment part 92 of the user. The adhesive layer 51 may be adhered to the body portion 94 around the treatment part 92 when the treatment part 92 of the user is covered by the recession 11 of the banding portion 1, thereby improving the air-tightness between the banding portion 1 and the body portion 94.

Figure 7:
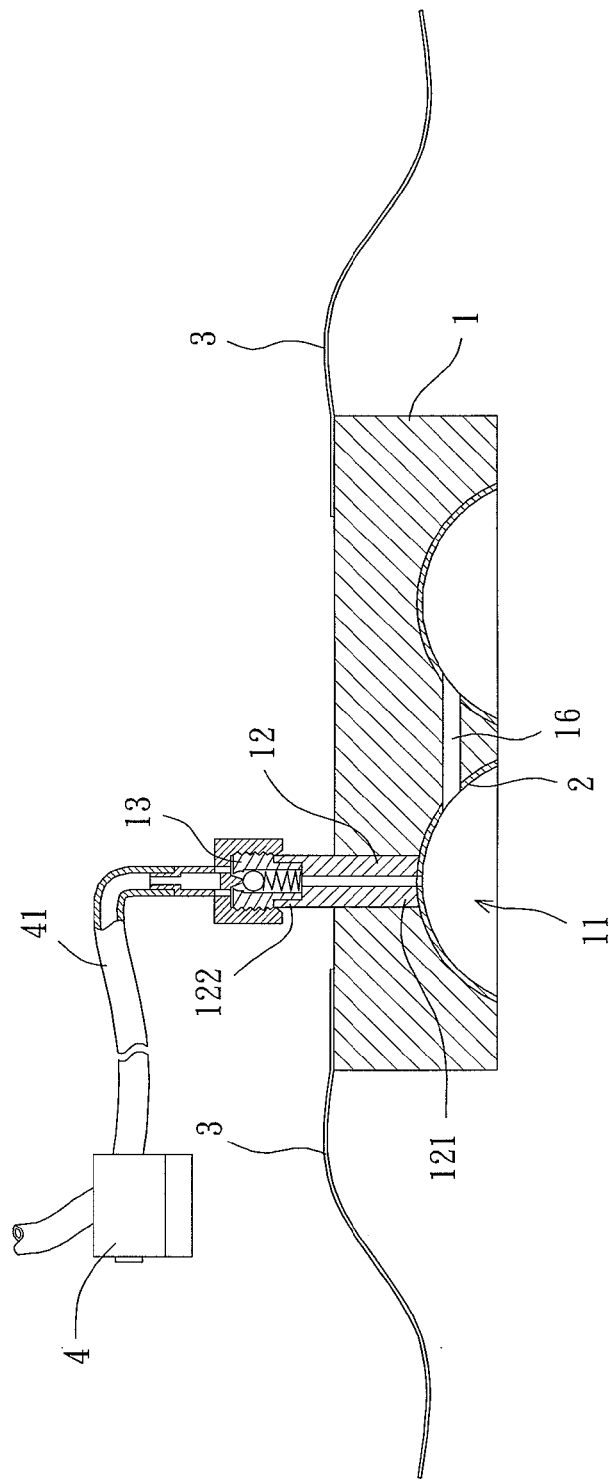
FIG. 7 shows a side cross sectional view of the negative pressure bandage according to a third embodiment of the invention.

Referring to FIGS. 7, a negative pressure bandage is disclosed according to a third embodiment of the present invention. In comparison with the first embodiment, what is different is that the banding portion 1 includes two recessions 11 formed in one side of the banding portion 1. In addition, the banding portion 1 further includes a channel 16 formed between the two recessions 11 to which two ends of the channel 16 are respectively connected. When the decompressing device 4 is operated, the pressure in the two recessions 11 is reduced to a desired level smaller than the atmospheric pressure at the same time. Therefore, the present invention can impart a negative pressure to the treatment part 92 of the user.

Figure 8:
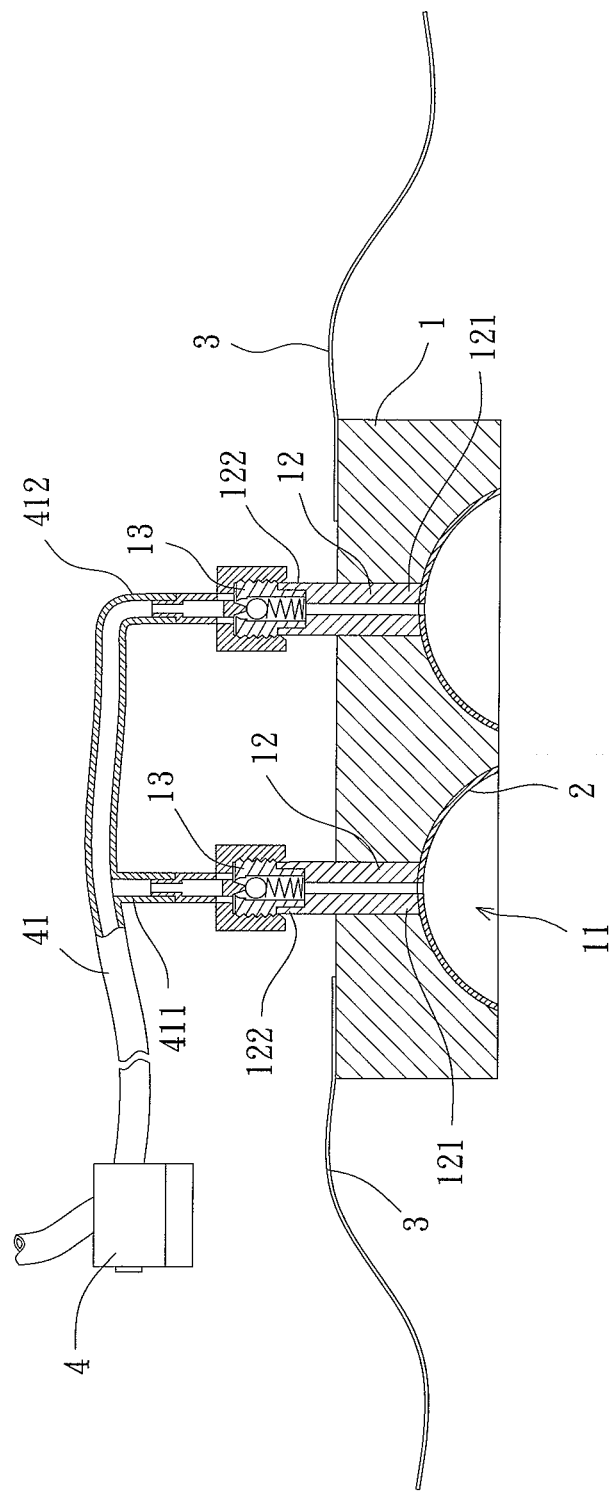
FIG. 8 shows a side cross sectional view of the negative pressure bandage according to a fourth embodiment of the invention.

Referring to FIGS. 8, a negative pressure bandage is disclosed according to a fourth embodiment of the present invention. In comparison with the first embodiment, what is different is that the banding portion 1 includes two recessions 11 formed in one side of the banding portion 1, two tubes 12 having the first end 121 and the second end 122, and two check valves 13 mounted in the second end 122 of the two tubes 12 respectively. Each first end 121 of the tubes 12 is connected to a respective one of the two recessions 11. Furthermore, the conduit 41 of the decompressing device 4 has a first terminal 411 and a second terminal 412, with the first terminal 411 being connected to one of the two check valve 13 and the second terminal 412 being connected to the other check valve 13. Air in the recession 11 is drawn out of the recession 11 to reduce the pressure in the recession 11. Therefore, the present invention can impart a negative pressure to the treatment part 92 of the user.

Thus since the invention disclosed herein may be embodied in other specific forms without departing from the spirit or general characteristics thereof, some of which forms have been indicated, the embodiments described herein are to be considered in all respects illustrative and not restrictive. The scope of the invention is to be indicated by the appended claims, rather than by the foregoing description, and all changes which come within the meaning and range of equivalency of the claims are intended to be embraced therein.

What is claimed is:

1. A negative pressure bandage comprising: a banding portion including at least one recession having a shape and formed in one side of the banding portion, at least one tube having a first end and a second end, and at least one check valve mounted in the second end of the tube, with the first end of the tube connected to the recession, with the at least one recession having an inner surface defining an empty space in the banding portion having an opening on the one side;

at least one infiltration arranged on the inner surface of the recession of the banding portion;

at least one fixing member fixing the banding portion to a treatment part;

wherein the at least one recession includes first and second recessions, wherein the pressure bandage further comprises a channel formed in the banding portion spaced from the one side between the first and second recessions, with first and second ends of the channel being connected with the two recessions respectively.

2. The negative pressure bandage as claimed in claim 1, wherein the recession further includes an extending groove formed in the one side and on an annular periphery of the recession at the one side of the banding portion, with the infiltration arranged on the inner surface of the recession and the extending groove.

3. The pressure bandage as claimed in claim 1, wherein the banding portion is made of a shapeable sponge or an elastic bandage in order to form any desired shape and size.

4. The pressure bandage as claimed in claim 1, wherein the fixing member includes two straps respectively having a hook fastener and a loop fastener releasably engaged with the hook fastener, wherein the two straps wrap around a body portion.

5. The pressure bandage as claimed in claim 1, wherein he number of the at least one tube is two and the number of the at least one check valve is two, with the two check valves being mounted in the second ends of the two tubes respectively, with each of the tubes being connected to a respective one of the first recession and the second recession.

6. The pressure bandage as claimed in claim 1, wherein the infiltration includes an adhesive layer adhered to a body portion around the treatment part.

* * * * *